US009849154B2

(12) United States Patent
Castex-Rizzi et al.

(10) Patent No.: US 9,849,154 B2
(45) Date of Patent: Dec. 26, 2017

(54) SYNERGISTIC COMBINATION OF ALANINE-GLUTAMINE, HYALURONIC ACID AND OAT EXTRACT AND THE USE THEREOF IN A COMPOSITION INTENDED FOR HEALING WOUNDS AND REPAIRING SKIN LESIONS

(71) Applicant: PIERRE FABRE DERMO-COSMETIQUE, Boulogne-Billancourt (FR)

(72) Inventors: Nathalie Castex-Rizzi, Colomiers (FR); Hélène Duplan, Auzeville Tolosan (FR); Corinne Dechelette, Rabastens (FR); Laetitia Bonzom, Toulouse (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 80 days.

(21) Appl. No.: 14/777,989

(22) PCT Filed: Apr. 10, 2014

(86) PCT No.: PCT/EP2014/057224
§ 371 (c)(1),
(2) Date: Sep. 17, 2015

(87) PCT Pub. No.: WO2014/167039
PCT Pub. Date: Oct. 16, 2014

(65) Prior Publication Data
US 2016/0303181 A1    Oct. 20, 2016

(30) Foreign Application Priority Data

Apr. 10, 2013 (FR) ..................................... 13 53231

(51) Int. Cl.
| A61K 38/05 | (2006.01) |
| A61K 36/899 | (2006.01) |
| A61K 31/728 | (2006.01) |
| A61K 9/00 | (2006.01) |
| A61K 9/107 | (2006.01) |
| A61L 15/28 | (2006.01) |
| A61L 15/32 | (2006.01) |
| A61L 15/44 | (2006.01) |

(52) U.S. Cl.
CPC ............ *A61K 38/05* (2013.01); *A61K 9/0014* (2013.01); *A61K 9/107* (2013.01); *A61K 31/728* (2013.01); *A61K 36/899* (2013.01); *A61L 15/28* (2013.01); *A61L 15/32* (2013.01); *A61L 15/44* (2013.01)

(58) Field of Classification Search
CPC ...................................................... A61K 36/00
See application file for complete search history.

(56) References Cited

U.S. PATENT DOCUMENTS 6,368,579 B1    4/2002 Barr

FOREIGN PATENT DOCUMENTS

| CN | 101816620 A | * | 9/2010 | |
| FR | 2 926 461 A1 | | 7/2009 | |
| FR | 2926461 A1 | * | 7/2009 | ............... A61K 8/44 |
| FR | 2 977 494 A1 | | 1/2013 | |
| JP | 2012240993 A | * | 12/2012 | |
| WO | WO 2010/054879 A2 | | 5/2010 | |

OTHER PUBLICATIONS

Pavicic et al, Efficacy of cream-based novel formulations of hyaluronic acid of different molecular weights in anti-wrinkle treatment. Journal of Drugs in Dermatology (2011), 10(9), 990-1000.*
French Search Report dated Sep. 11, 2013, for French Application No. 1353231.
International Search Report dated Jun. 16, 2014, for International Application No. PCT/EP2014/057224 with the English translation.
McMillan et al., "Epidermal basement membrane zone components: ultrastructural distribution and molecular interactions," Journal of Dermatological Science, vol. 31, 2003, pp. 169-177.
Santoro et al., "Cellular and molecular facets of keratinocyte reepithelization during wound healing," Experimental Cell Research, vol. 304, 2005 (Available onloine Dec. 8, 2004), pp. 274-286.
Steffensen et al., "Proteolytic Events of Wound-Healing-Coordinated Interactions Among Matrix Metalloproteinases (MMPs), Integrins, and Extracellular Matrix Molecules," Crit. Rev. Oral Biol. Med., vol. 12, No. 5, 2001, pp. 373-398.
Szabo et al., "Cell-Density-Regulated Chemotactic Responsiveness of Keratinocytes in Vitro," The Journal of Investigative Dermatology, vol. 117, No. 5, Nov. 2001, pp. 1083-1090.
Werner et al., "Regulation of Wound Healing by Growth Factors and Cytokines," Physiol Rev, vol. 83, 2003, pp. 835-870.
International Search Report issued in PCT/EP2014/057224 dated Jun. 16, 2014.

* cited by examiner

*Primary Examiner* — Qiuwen Mi
(74) *Attorney, Agent, or Firm* — Birch, Stewart, Kolasch & Birch, LLP

(57) ABSTRACT

The present invention concerns a combination comprising the dipeptide L-alanyl-L-glutamine, hyaluronic acid or one of the salts of same and an oat extract, advantageously intended for healing wounds and repairing skin lesions.

9 Claims, 1 Drawing Sheet

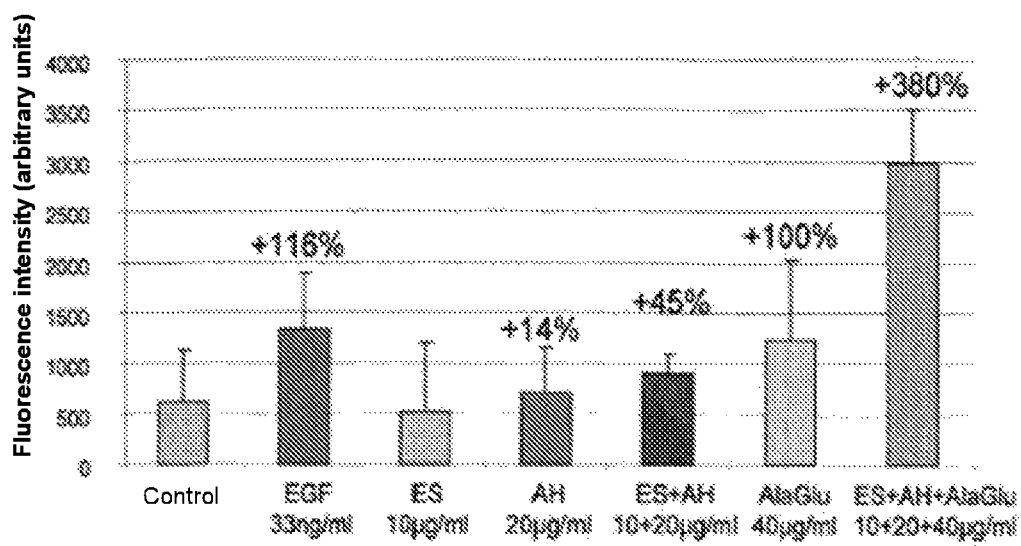
Single figure

SYNERGISTIC COMBINATION OF ALANINE-GLUTAMINE, HYALURONIC ACID AND OAT EXTRACT AND THE USE THEREOF IN A COMPOSITION INTENDED FOR HEALING WOUNDS AND REPAIRING SKIN LESIONS

The present invention concerns a synergistic combination comprising the dipeptide L-alanyl-L-glutamine, hyaluronic acid or one of the salts of same and an oat extract, advantageously intended for healing wounds and repairing skin lesions.

Healing is a series of local defence phenomena, which occur after an aggression: injury, burn, dermatological act, surgical intervention. Numerous active products from blood and tissue are released during these phenomena: enzymes, various proteins, histamine, etc. Healing comprises several steps, the first of which is the coagulation of the blood, stopping bleeding. White blood cells from the blood eliminate the dead cells. Then the surviving cells proliferate and give rise to new tissue, the appearance of which depends on the location of the lesion.

Healing depends on several factors, particularly nutritional, metabolic, endocrinal or medicational; delays in healing are observed in malnourished or elderly subjects, or in the case of prolonged taking of corticoids. With age, the process of improving the healing and the recovery of skin lesions in fact becomes less effective, the process is slower.

There still exists a need to propose novel compositions for rapid and aesthetic repair of skin lesions.

The pharmacological properties of the dipeptide L-alanyl-L-glutamine administered by oral route described in the literature are numerous.

Among others, the dipeptide L-alanyl-L-glutamine is used per os as supplement for sports people to facilitate recovery after effort and after a surgical intervention to reduce hospitalisation time.

This dipeptide is also recommended in parenteral nutrition as a complement to a standard solution of amino acids or other mixtures used in parenteral nutrition in resuscitation patients requiring a glutamine intake.

In the present invention, the inventors have shown in a surprising manner that the dipeptide L-alanyl-L-glutamine used by topical route has biological activity on the skin, based on its regenerative properties: action on the migration of keratinocytes.

Furthermore, the inventors have also shown that this activity is greatly amplified when this dipeptide is combined with an oat extract and hyaluronic acid.

In particular, the inventors have demonstrated the existence of a synergy between the three components, which are oat extract and more specifically oat seedling extract, hyaluronic acid or one of the salts of same and L-alanyl-L-glutamine, on the migration of keratinocytes. This activity is particularly interesting in tissue regeneration and the healing of skin lesions.

In fact, the migration of epithelial cells is an important step of the development and the process of tissue repair, such as embryogenesis and healing.

The mechanisms of initiation, coordination and stoppage of the movements of cells are not completely elucidated, however the vital role of cell migration is well established. Several agents capable of stimulating this cellular process have been characterised, such as certain matricial or cytoplasmic proteins (SANTORO M M., GAUDINO G., Cellular and molecular facets of keratinocyte reepithelization during wound healing. EXP. CELL. RES. 304(1): 274-286, 2005) (WERNER S., GROSE R. Regulation of wound healing by growth factors and cytokines. PHYSIOL. REV. 83(3): 835-870, 2003) (STEFFENSEN B., AKKINEN L., LARIAVA H. Proteolytic events of wound healing-coordinated interactions among matrix metallopteinases (MMPs), integrins, and extracellular matrix molecules. CRIT. REV. ORAL BIOL. MED. 12(5): 373-398, 2001).

During skin healing and in chronic dermatological inflammatory affections, keratinocytes are "activated" in order to undertake the process of migration. The cells then see their phenotype influenced by interactions with the extracellular matrix on the one hand and by cell-cell interactions on the other hand (MCMILLAN J. R., AKIYAMA M., SHIMIZU H. Epidermal basement membrane zone component: ultrastructural distribution and molecular interactions. J DERM SC. 31:169-177, 2003). Keratinocytes of the basal layer of the banks of a wound migrate onto the wound and cover it. In fact, keratinocytes are activated on contact with fibronectin, interstitial dermal collagen (type 1), collagen IV and laminin 5 of the basal lamina. They are also regulated by certain polypeptide growth factors such as TGFβ, TGFα and EGF. In addition, cytokines (IL1, TNFα) and chemokines (RANTES and IL8) also contribute to increasing the speed of re-epithelisation of a wound, following keratinocyte activation (SZABO I., WETZEL M. A., ROGERS T J. Cell-Density-Regulated Chemotactic Responsiveness of Keratinocytes In Vitro. J INVEST DERMATOL 117:1083-1090, 2001.

CAPTION FOR THE APPENDED FIGURE

The single appended FIGURE illustrates the effect of oat seedling extract/hyaluronic acid and L-alanyl-L-glutamine and combinations thereof on the migration of keratinocytes.

The subject matter of the present invention is a combination comprising L-alanyl-L-glutamine, hyaluronic acid or one of the salts of same and an oat extract.

The term "L-alanine" refers to (S)-2-aminopropanoic acid, also called α-aminopropionic acid. L-alanine is a neutral amino acid with slightly apolar and hydrophobic properties.

The term "L-glutamine" refers to 2-aminoglutaramic acid. L-glutamine is a semi-essential, polar non-charged and hydrophilic amino acid.

In a particular embodiment of the invention, the combination comprises a hyaluronic acid or one of the salts of same, of high molecular weight. Preferably, the molecular weight will be comprised between 50,000 and 750,000 Da, and preferably between 250,000 and 450,000 Da.

The hyaluronic acid salt will preferentially be sodium hyaluronate.

According to a mode of execution of the invention, the hyaluronate salt will have a molecular weight comprised between 50,000 and 750,000 Da, and preferably between 250,000 and 450,000 Da.

In an embodiment of the invention, the oat extract is obtained from oat seedlings, and preferentially as described in WO 2010/054879.

"Oat seedlings" is taken to mean within the sense of the present invention oats before ear emergence, that is to say at the stage after germination (around 2 weeks to 2 months after germination) during the stage from stem elongation up to ear emergence not included. "Stem elongation" designates the growth phase which corresponds to the elongation of the stem and to the rise of the ear in formation, before flowering. Secondary metabolites are described in patent application WO2010/054879 as components of an oat seedling extract: flavonoids and saponins of avenacoside type. Said extract is characterised by the presence of 2 to 15% of flavonoids and 0.2 to 2% of A and B avenacosides.

The method of preparation of the oat extract may be as follows:
  drying and grinding parts of oats, preferably oat seedlings, extraction in organic solvent chosen from the group constituted of ketones, esters, C1 to C4 alcohols and mixtures in any miscible proportion of these solvents, and
  centrifugation or filtration.

Advantageously, the organic solvent of the method according to the invention is chosen from the group constituted of acetone, methyl ethyl ketone, methyl isobutyl ketone, ethyl acetate, a C1 to C4 alcohol and a mixture in any miscible proportion of these solvents.

The pomace obtained by the extraction step is then separated from the extract by centrifugation or filtration and the solution may be more or less concentrated until a dry extract is obtained.

According to a mode of execution of the invention, a support may be added during the drying step in weight proportions compared to extracted dry matter being able to vary from 1 to 75%. The support may be a sugar such as maltodextrin, lactose, silica or any other cosmetologically acceptable support.

In another embodiment of the invention, the solution is concentrated so as to obtain a wort comprising from 60 to 80% of dry matter, and preferably 70% of dry matter.

In a particular embodiment, the combination according to the invention is characterised in that the hyaluronic acid/oat extract/L-alanyl-L-glutamine weight ratio is respectively comprised between 2/1/3 and 2/1/5.

In another mode of execution, the hyaluronic acid, oat seedling extract and L-alanyl-L-glutamine ratio is a weight ratio respectively of 2/1/4.

In another preferred embodiment, the composition according to the invention comprises a hyaluronic acid/oat seedling extract/L-alanyl-L-glutamine ratio respectively of 2/1/4.

Another subject matter of the present invention concerns a novel dermatological or cosmetic composition intended to accelerate skin repair in order to re-establish the integrity and the quality of the skin.

The composition according to the invention comprises as dermatological or cosmetic active ingredient the aforementioned combination of hyaluronic acid, oat extract and L-alanyl-L-glutamine and further comprises at least one dermatologically or cosmetically acceptable excipient.

In a preferred embodiment of the invention, the composition is intended for topical application.

The dermatologically (pharmaceutically) or cosmetically compatible excipients may be any excipient among those known to those skilled in the art with a view to obtaining a composition for topical application in the form of a milk, of a cream, of a balm, of an oil, of a lotion, of a gel, of a foaming gel, of an ointment, of a spray, etc.

In a preferred embodiment, the composition will be in the form of a cream, of an ointment.

In an embodiment, the composition according to the invention comprises at least one other active ingredient.

"Active ingredient" according to the invention is taken to mean any substance having dermatological or cosmetic properties.

This other active ingredient could in particular be selected from the group comprising healing, soothing, antipruritic, anti-ageing, anti-wrinkling, anti-radical, anti-UV agents, agents stimulating the synthesis of dermal macromolecules or energy metabolism, moisturising, antibacterial, antifungal, anti-inflammatory, anaesthetic agents.

Preferentially, healing and/or soothing agents will be used.

Finally, another subject matter of the present invention relates to the use of compositions based on the combination of hyaluronic acid, oat extract and L-alanyl-L-glutamine for the treatment and the healing of skin lesions.

The present invention relates, moreover, to a combination of hyaluronic acid, oat seedling extract and L-alanyl-L-glutamine according to the invention for the preparation of a composition intended to favour keratinocyte migration.

The composition according to the invention is intended for the care of damaged skin:
  following invasive acts/treatments: surgical acts (exeresis, shavings) with or without suture, cryotherapy, ablation laser, medium or heavy peelings, mosotherapy, curettage.
  in post traumatics during superficial cuts or burns.
  following superficial (non-invasive) acts requiring a healing product which accelerates skin recovery, which can be used in the long term (up to complete repair of the skin).
  following a slight exterior alteration: superficial grazes, sunburn.

The treatment of lesions of the skin and the mucous membranes according to the invention could in particular comprise the treatment of cuts, sutures, grazes, scratches, scrapes, post-surgery scars or post-aesthetic dermatological interventions, superficial burns, sunburn.

The present invention relates, furthermore, to the use of a cosmetic composition according to the invention intended to improve skin healing and repair.

The invention will be better understood on reading the results below which illustrate it without limiting the scope thereof.

Pharmacological Evaluation on the Migration of Keratinocytes

The objective of this test was to evaluate the effect of hyaluronic acid, oat seedling extract, L-alanyl-L-glutamine and combinations thereof on the migration of keratinocytes using the Oris Cell Migration Assay kit (Platypus Technologies).

Biological Material

The spontaneously immortalised HaCaT human keratinocyte line, frequently cited as reference model in the literature was used.

Cell Migration Protocol

The protocol used for the study of cell migration is based on the use of a 96 well kit, the Oris Cell Migration Assay (Platypus technologies—TEBU), enabling the miniaturisation and the quantification of this cellular process.

The principle of this test consists in studying cell migration towards the centre of the wells of the 96 well plate. It consists in placing a stopper in the wells, in order to create a 2 mm diameter detection zone. Then removing the stoppers once cells have properly adhered to the surface around them, and thus to enable cells to migrate towards the detection zone. The plates without stoppers and with the active ingredients are incubated at 37° C. for 24 hours in DMEM (Dulbecco's Modified Eagle Medium) 0% FCS (foetal calf serum). The quantity of cells situated in the zone where the stopper was is analysed in order to evaluate the migration of the cells. A mask makes it possible to visualise and to count uniquely the cells situated in this zone. For each condition, the average is determined on 6 to 8 wells.

The cells were incubated in FCS-free medium.
The Products Tested
  EGF: 33 ng/ml,
  oat seedling extract: 10 or 30 µg/ml,
  Preparation of the Extract:
  Extracting 10 g of ground seedlings with 100 ml of acetone/water (80/20) (v/v) extraction solvent.
  Filtering and rinsing the pomace with the extraction solvent.
  Evaporating the acetone and taking up the aqueous phase.
  Filtering. Concentration by drying until a dry extract is obtained.
  sodium hyaluronate (molecular weight 250-450 kDa): 20 or 60 µg/ml,
  L-alanyl-L-glutamine: 40 or 90 µg/ml.
Analysis of the Results
  The Results are Expressed:
  In fluorescence intensity (FI), proportional to the quantity of cells having migrated.
  In percentage activity compared to the control 0% FCS.

$$\frac{FI\ treated}{FI\ control\ 0\%\ FCS} \times 100$$

Statistical Analyses

Statistical analyses by the Dunnett test were carried out on the crude migration values. This test then gives "p value" values characterising the significance of the results obtained for different conditions. The degree of significance was fixed at p<0.05 (* significant)
  P<0.01 (** very significant)
  P<0.001 (*** highly significant)
  P>0.05 (not significant).

Results

The results at different concentrations of the effect of oat seedling extract, hyaluronic acid and L-alanyl-L-glutamine, alone or in combination on the migration of keratinocytes are indexed in tables 1 and 2 then represented in the single FIGURE. The fluorescence intensity values represented on this curve correspond to an average of 6 to 8 measurements carried out during an experiment representative of 3 independent manipulations.

In the presence of DMEM and 0% FCS, the positive control of the EGF experiments indeed induces the migration of keratinocytes. In these experimental conditions, oat seedling extract (10 or 30 µg/ml) alone and hyaluronate (20 or 60 µg/ml) alone did not have any significant effect on the migration of keratinocytes. Their combination seems on the other hand to show a trend to increase migration: +45% or +27% compared to the control as a function of the concentrations tested (tables 1 and 2).

L-alanyl-L-glutamine alone induces the migration of keratinocytes in a concentration-dependent manner. These inductions are even more important than with the EGF positive control. The combinations of the 3 active ingredients—oat seedling extract, hyaluronic acid and L-alanyl-L-glutamine—induce in a very important and statistically significant manner the migration of keratinocytes. Tables 1 and 2 and FIG. 1 show that these inductions are statistically significant compared to the control, but they are also statistically significant compared to oat seedling extract and to hyaluronic acid alone or compared to their combination.

The appended FIG. 1 illustrates the effect of the dry extract of oat seedlings (ES), hyaluronic acid (AH), L-alanyl-L-glutamine (Ala-Glu) and combinations thereof on the migration of keratinocytes. The percentages correspond to additional activity percentages compared to the control.

TABLE 1

Effects of the dry extract of oat seedlings (ES), hyaluronic acid (AH), L-alanyl-L-glutamine (A-G) and combinations thereof on the migration of keratinocytes.

| Groups | Concentration | Average ± SD | % Migration |
|---|---|---|---|
| Control | | 1850± | 100 |
| EGF | 33 ng/ml | 2569± | 216 |
| Oat seedling dry extract (ES) | 10 µg/ml | 1748 ± 681 | |
| Hyaluronic acid (AH) | 20 µg/ml | 1939 ± 438 | 114 |

TABLE 1-continued

Effects of the dry extract of oat seedlings (ES), hyaluronic acid (AH), L-alanyl-L-glutamine (A-G) and combinations thereof on the migration of keratinocytes.

| Groups | Concentration | Average ± SD | % Migration |
|---|---|---|---|
| ALANYL GLUTAMINE | 40 µg/ml | 2471 ± 788 | 200 |
| ES + AH | 10 + 20 µg/ml | 2129± | 145 |
| ES + AH + A-G | 10 + 20 + 40 | 4211± | 480 ** |

SD: Standard deviation,
** p < 0.01 versus control.

TABLE 2

Effects of the dry extract of oat seedlings (ES), hyaluronic acid (AH), L-alanyl-L-glutamine (A-G), and combinations thereof on the migration of keratinocytes.

| Groups | Concentration | Average ± SD | % Migration |
|---|---|---|---|
| Control | | 1729 ± 384 | 100 |
| EGF | 33 ng/ml | 3553 ± 1556 | 301 * |
| ES | 30 µg/ml | 1386 ± 226 | 62 |
| AH | 60 µg/ml | 1735 ± 488 | 101 |
| A-G | 90 µg/ml | 2586 ± 1092 | 194 |
| ES + AH | 30 + 60 µg/ml | 1152 ± 541 | 127 |
| ES + AH + A- | 30 + 60 + 90 µg/ml | 2877 ± 1024 | 317 ** |

SD: Standard deviation,
* p < 0.05,
** p < 0.01 versus control.

Consequently a combination of oat seedling extract, hyaluronic acid or one of the salts of same and L-alanyl-L-glutamine increases in a synergic manner the migration of keratinocytes. These results confirm the interest of using such a combination in a dermatological or cosmetic healing composition.

EXAMPLE OF COMPOSITION: OIL IN WATER EMULSION

|  |  | Percentage | Function |
|---|---|---|---|
| Aqueous phase | Water | QS100% |  |
|  | Oat extract obtained following extraction with acetone, filtration, and concentration until a wort with 70% of dry matter is obtained | 0.1-3% | Active ingredient |
|  | Sodium hyaluronate of molecular weight 250-400 kDa | 0.05-1% | Active ingredient |
|  | L-Alanyl-L-glutamine | 0.1-1% | Active ingredient |
|  | Glycerine | 1-30% | Humectant |
|  | Hexylene glycol | 0.1-7% | Glycol |
| Lipophilic phase | Cetearyl glucoside | 0.1-1% | Emulsifier |
|  | Cetearyl alcohol | 0.9-4% | Emulsifier |
|  | Stearic acid | 0.5-4% | Consistency factor |
|  | Glyceryl stearate | 0.1-4% | Consistency factor |
|  | Vegetable oil | 0.1-10% | Emollient |
|  | *Butyrospermum Parkii* (Shea) Butter | 0.1-10% | Emollient |
|  | Silicone | 0.1-5% | Emollient |

The invention claimed is:

1. A combination comprising L-alanyl-L-glutamine, hyaluronic acid or one of the salts of same and an oat extract, wherein the oat extract is obtained from oat seedlings and wherein the hyaluronic acid/oat seedling extract/L-alanyl-L-glutamine weight ratio is respectively between 2/1/3 and 2/1/5.

2. The combination according to claim 1, wherein the hyaluronic acid is in the form of fragments of sodium hyaluronate.

3. The combination according to claim 2, wherein the molecular weight of the fragments of hyaluronate is between 50,000 and 750,000 Da.

4. The combination according to claim 1, wherein the hyaluronic acid/oat seedling extract/L-alanyl-L-glutamine ratio is a weight ratio respectively of 2/1/4.

5. A dermatological or cosmetic composition comprising as active ingredient a combination according to claim 1, with at least one dermatologically or cosmetically acceptable excipient.

6. A method for favouring keratinocyte migration, said method comprising the topical application of an effective amount of the combination according to claim 1 to a person in need thereof.

7. A method for treating skin lesions, said method comprising the topical application to the skin of an effective amount of the combination according to claim 1 to a person in need thereof.

8. A method for improving skin healing and recovery, said method comprising the topical application to the skin of an effective amount of the combination according to claim 1 to a person in need thereof.

9. A method for treating cuts, sutures, grazes, scratches, scrapes, post-surgery or post-aesthetic dermatological interventions scars, superficial burns, or sunburn, said method comprising the administration to a person in need thereof of the dermatological or cosmetic composition according to claim 5.

* * * * *